United States Patent
Wang et al.

(10) Patent No.: US 10,743,091 B1
(45) Date of Patent: Aug. 11, 2020

(54) MOBILE BIOMETRIC-DATA HUB

(71) Applicant: BioIntelliSense, Inc., Redwood City, CA (US)

(72) Inventors: David Jonq Wang, Palo Alto, CA (US); Henry WeiKang Leung, Sunnyvale, CA (US); James R. Mault, Evergreen, CO (US)

(73) Assignee: BIOINTELLISENSE, INC., Redwood City, CA (US)

( * ) Notice: Subject to any disclaimer, the term of this patent is extended or adjusted under 35 U.S.C. 154(b) by 0 days.

(21) Appl. No.: 16/395,052

(22) Filed: Apr. 25, 2019

(51) Int. Cl.
| | |
|---|---|
| *H04Q 9/00* | (2006.01) |
| *A61B 5/117* | (2016.01) |
| *A61B 5/00* | (2006.01) |
| *G16H 40/67* | (2018.01) |
| *G16H 10/60* | (2018.01) |
| *H04B 1/38* | (2015.01) |
| *H04W 84/18* | (2009.01) |

(52) U.S. Cl.
CPC .............. *H04Q 9/00* (2013.01); *A61B 5/0022* (2013.01); *A61B 5/117* (2013.01); *A61B 5/7221* (2013.01); *G16H 40/67* (2018.01); *H04Q 2209/40* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 9,687,195 B2 * | 6/2017 | Sims ............... | A61B 5/1135 |
| 2019/0090135 A1 * | 3/2019 | Milevski .......... | H04W 12/08 |
| 2019/0090812 A1 * | 3/2019 | Martin ............. | A61B 5/1038 |

OTHER PUBLICATIONS

Amazon "Withings | Body+—Smart Body Composition Wi-Fi Digital Scale with smartphone app" <https://www.amazon.com/Withings-Nokia-Body-Composition-smartphone/dp/B071CMGR9C/ref=sr_1_2_sspa?keywords=wifi%2Bscale&qid=1562861021&s=gateway&sr=8-2-spons&th=1> retrieved Jul. 11, 2019 10pgs.
Apple "iPhone 8" available on Apple.com <https://www.apple.com/shop/buy-iphone/iphone-8> retrieved Jul. 11, 2019 4pgs.

* cited by examiner

*Primary Examiner* — Curtis A Kuntz
*Assistant Examiner* — Jerold B Murphy
(74) *Attorney, Agent, or Firm* — Maschoff Brennan (57) ABSTRACT

According to an aspect of an embodiment, a method may include obtaining, at a mobile biometric-data hub, a first biometric reading of a user. The method may also include, based on the first biometric reading, associating the mobile biometric-data hub with the user. The method may also include wirelessly receiving, at the mobile biometric-data hub, a second biometric reading from a biometric sensor distinct from the mobile biometric-data hub. The method may also include determining that the second biometric reading is of the user. The method may also include, based on the second biometric reading being of the user and based on the association between the mobile biometric-data hub and the user, tagging the second biometric reading with an identifier of the user. The method may also include communicating the tagged second biometric reading from the mobile biometric-data hub to a network-attached device.

19 Claims, 4 Drawing Sheets

MOBILE BIOMETRIC-DATA HUB

FIELD

Some embodiments described herein generally relate to a mobile biometric-data hub.

BACKGROUND

To gain information about the health of a person, various measurements of the person may be taken. Various biometric sensing devices may take the various measurements. The various biometric sensing devices may be dispersed and the measurements may be taken at discrete times.

The subject matter described in the present disclosure is not limited to embodiments that solve any disadvantages or that operate only in environments such as those described above. Rather, this background is only provided to illustrate one example technology area where some embodiments described in the present disclosure may be practiced. Unless otherwise indicated herein, the materials described herein are not prior art to the claims in the present application and are not admitted to be prior art by inclusion in this section.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One embodiment of the present disclosure may include a method that includes obtaining, at a mobile biometric-data hub, a first biometric reading of a user. The method may also include, based on the first biometric reading, associating the mobile biometric-data hub with the user. The method may also include wirelessly receiving, at the mobile biometric-data hub, a second biometric reading from a biometric sensor distinct from the mobile biometric-data hub. The method may also include determining that the second biometric reading is of the user. The method may also include, based on the second biometric reading being of the user and based on the association between the mobile biometric-data hub and the user, tagging the second biometric reading with an identifier of the user. The method may also include communicating the tagged second biometric reading from the mobile biometric-data hub to a network-attached device.

Another embodiment of the present disclosure may include a mobile biometric-data hub that includes a first biometric sensor configured to take a first biometric reading of a user. The mobile biometric-data hub may also include a communication interface configured to wirelessly receive a second biometric reading of the user from a second biometric sensor. The mobile biometric-data hub may also include a processor configured to execute instructions to perform operations. The operations may include associating the mobile biometric-data hub with the user based on the first biometric reading. The operations may also include determining that the second biometric reading is of the user. The operations may also include, based on the second biometric reading being of the user and based on the association between the mobile biometric-data hub and the user, tagging the second biometric reading with an identifier of the user. The operations may also include directing the communication interface to communicate the tagged second biometric reading to a network-attached device. The mobile biometric-data hub may also include a data storage configured to store the instructions and the tagged second biometric reading.

Another embodiment of the present disclosure may include a system including a biometric sensing device. The biometric sensing device may include a first biometric sensor configured to take a first biometric reading of a user and a first communication interface configured to wirelessly transmit the first biometric reading. The system may also include a mobile biometric-data hub. The mobile biometric-data hub may include a second communication interface configured to wirelessly receive the first biometric reading. The mobile biometric-data hub may also include a processor configured to execute instructions to perform operations. The operations may include determining that the first biometric reading is of the user. The operations may also include, based on the first biometric reading being of the user, tagging the first biometric reading with an identifier of the user. The operations may also include directing the second communication interface to wirelessly transmit the tagged first biometric reading. The mobile biometric-data hub may also include a data storage configured to store the instructions and the tagged first biometric reading. The system may also include a network-attached device. The network-attached device may include a third communication interface configured to wirelessly receive the tagged first biometric reading and a fourth communication interface configured to communicate the tagged first biometric reading to a separate computing device over a communication network.

Additional features and advantages of the present disclosure will be set forth in the description which follows, and/or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Some example embodiments described herein generally relate to a mobile biometric-data hub that may collect biometric readings from various biometric sensors, validate that the biometric readings are of a particular person, and communicate the validated biometric readings to a separate network-attached device.

In one example operation, the mobile biometric-data hub may authenticate itself. For example, a particular person may wear the mobile biometric-data hub (e.g., a user of the mobile biometric-data hub), and the mobile biometric-data hub may take and store a signature biometric reading of the user using a biometric sensor using a biometric sensor that is part of the mobile biometric-data hub. As used herein a "person" may refer to any individual, while a "user" may refer to the particular person bearing (e.g., wearing or carrying) the mobile biometric-data hub. The signature biometric reading may be used later to verify that the user wearing the mobile biometric-data hub is the particular person for which the biometric signature was generated. For example, at a later time, the mobile biometric-data hub may obtain an authenticating biometric reading of the user of the mobile biometric-data hub from the biometric sensor used to generate the biometric signature, compare that reading to the biometric signature of the particular person taken previously, and based on similarity, authenticate itself and/or associate the mobile biometric-data hub with the particular person.

In some embodiments, the mobile biometric-data hub may validate that other readings from other sensors that are not part of the mobile biometric-data hub are of the particular person and may associate the other readings with the particular person. For example, the mobile biometric-data hub may wirelessly receive a biometric reading from a biometric sensor that is separate and distinct from the mobile biometric-data hub. Based on the authentication of the mobile biometric-data hub as being associated with the particular person, the mobile biometric-data hub may tag the biometric reading as being associated with the particular person.

The mobile biometric-data hub may store the tagged reading, e.g., until the mobile biometric-data hub is able to provide the tagged reading to a network-attached device. The network-attached device may store the tagged reading and/or communicate the tagged reading across a communication network to a separate computing device.

The term "biometric readings" may include measurements of a person, including such measurements as heart beat measurements, blood-sugar measurements, blood-pressure measurements, weight measurements, sound measurements including heartbeat and vocal measurements, movement measurements including gait measurements, sweat measurements, chemical measurements for example from sweat and/or sweat vapor, and electrical measurements for example galvanic skin response, among others.

Reference will now be made to the drawings to describe various aspects of some example embodiments of the disclosure. The drawings are diagrammatic and schematic representations of such example embodiments, and are not limiting of the present disclosure, nor are they necessarily drawn to scale.

Figure 1:
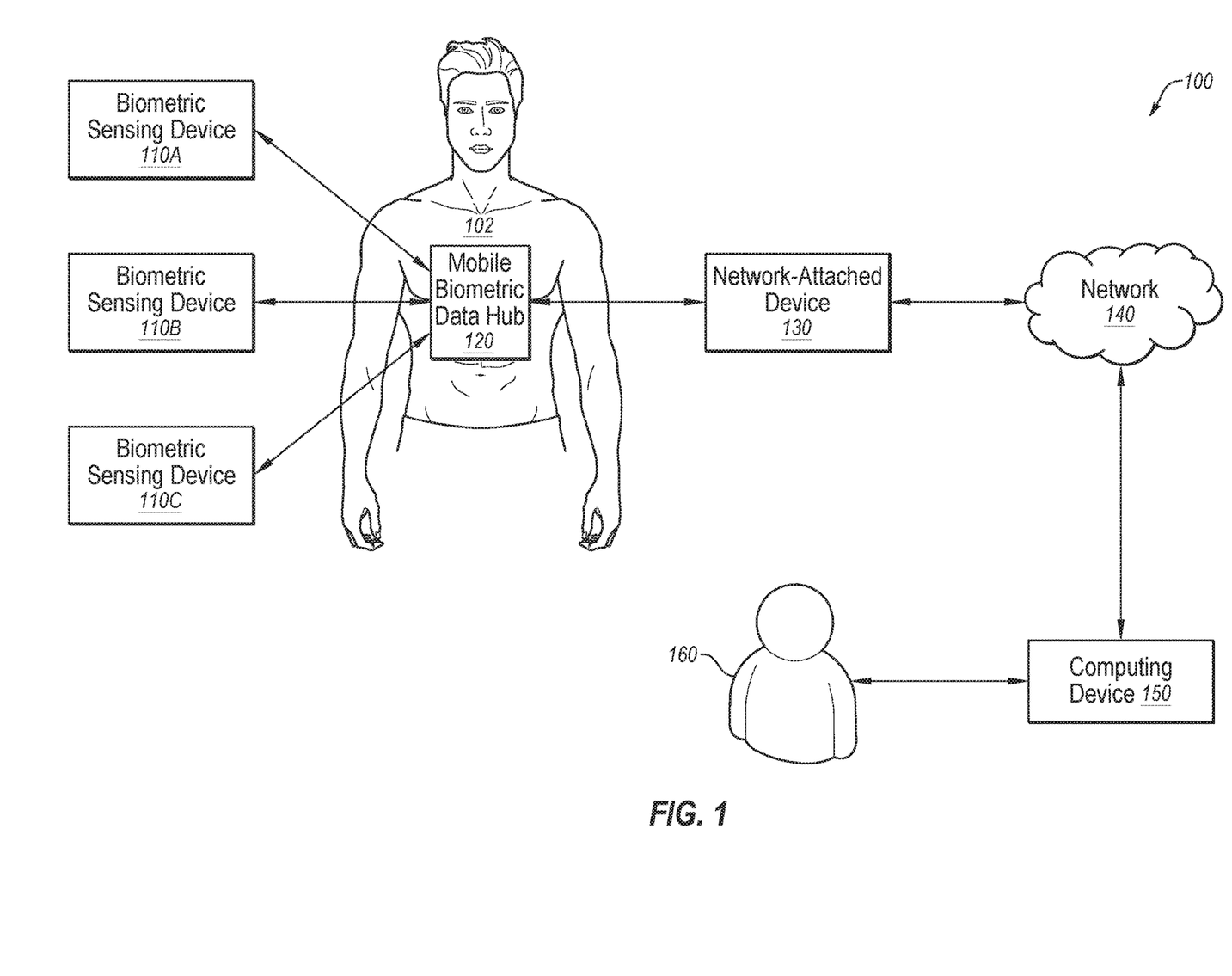
FIG. 1 illustrates an example environment in which some embodiments described herein can be implemented.

FIG. 1 illustrates an example environment 100 in which some embodiments described herein can be implemented according to at least one embodiment described in the present disclosure. The environment 100 may include a user 102, multiple biometric sensing devices 110, a mobile biometric-data hub 120, a network-attached device 130, a network 140, a computing device 150, and a third party 160. In FIG. 1, three biometric sensing devices 110 are illustrated, a first biometric sensing device 110A, a second biometric sensing device 110B, and a third biometric sensing device 110C (collectively referred to as the biometric sensing devices 110 and/or individually as biometric sensing device 110). Although three biometric sensing devices 110 are illustrated, the environment 100 may include any number of biometric sensing devices 110.

In operation, the mobile biometric-data hub 120 may authenticate itself (e.g., verify that the user 102 of the mobile biometric data hub 120 is a particular person) and/or associate itself with the user 102 (e.g. the particular person). Additionally, the mobile biometric data hub 120 may be configured to collect various biometric readings taken by the biometric sensing devices 110. Based on the authentication of the mobile biometric data hub 120 and based on a determination that the various biometric readings are of the user, the mobile biometric data hub 120 may be configured to tag the various biometric readings with an identifier of the user 102. Additionally or alternatively, the mobile biometric-data hub 120 may be configured to collect biometric readings that may have been taken of people other than the user 102. The mobile biometric-data hub 120 may communicate the collected biometric readings (including both the tagged biometric readings and the biometric readings of the other people) to the network-attached device 130, which may communicate the collected biometric readings over the network 140 to the computing device 150 and/or the third party 160.

The user 102 may be a person bearing (e.g., wearing or carrying) the mobile biometric-data hub 120 that may have biometric readings taken of them. The biometric readings may be taken with the active participation of the user 102, for example, the user 102 may prick a finger and apply blood to a sensor to obtain a blood-based biometric reading. Additionally or alternatively, the biometric readings may be taken passively with little or no involvement from the user, for example, a watch or wristband worn by the user may take a heart-rate-based or sweat-based biometric reading of the user.

In some embodiments, the user 102 may have created an account or login with a biometric monitoring service or using a biometric monitoring application or device. For example, the computing device 150 may store biometric information of the user 102 in association with an identifier, e.g., a username or identification number. Additionally or alternatively, the mobile biometric data hub 120 may store biometric information (e.g., biometric readings) of the user 102 in association with an identifier generated by the mobile biometric data hub 120 for the user 102. For example, the mobile biometric data hub 120 may obtain one or more biometric readings of the user 102 when the user 102 uses the mobile biometric data hub 120 for the first time. The mobile biometric data hub 120 may store the biometric readings as signature data that can be used to verify that the person using the mobile biometric data hub 120 is the user 102 at a later time. Additionally or alternatively, the mobile biometric data hub 120 may generate an identifier for the user 102. Thereafter, the mobile biometric data hub 120 may be configured to verify that any person using the mobile biometric data hub 120 is the user 102.

Each of the biometric sensing devices 110 may be configured to take one or more biometric readings of the user 102 and/or any other person. Additionally or alternatively, the biometric sensing devices may be configured to store and/or communicate the biometric readings to the mobile biometric-data hub 120.

In some embodiments, the biometric sensing devices 110 may be configured to store multiple biometric readings, including biometric readings which may be from multiple people. In these or other embodiments, the biometric sensing devices 110 may be configured to communicate the multiple biometric readings to the mobile biometric-data hub 120 e.g., for communication to the network-attached device 130. For example, a bathroom scale may be used by multiple different people, one of which may be the user 102 associated with the mobile biometric-data hub 120. The bathroom scale may be configured to store weight readings each time the bathroom scale is used. The bathroom scale may communicate the stored weight readings to the mobile biometric-data hub 120 when the mobile biometric-data hub 120 is communicatively coupled to the bathroom scale, (e.g., when the user 102 uses the bathroom scale). The communicated weight readings may include the reading just taken and/or other stored readings of the user 102 and/or other people. The mobile biometric-data hub 120 may be configured to communicate the weight readings to the network-attached device 130 which may communicate the weight readings to the computing device 150. The computing device 150 may allow the user 102, the multiple other people, and or the third party 160 to access weight data through another interface e.g., a web browser.

In some embodiments, the biometric sensing devices 110 may be configured to encrypt biometric readings. For example, the biometric sensing devices 110 may be configured to encrypt all biometric readings before storing the biometric readings and/or before communicating the biometric readings to the mobile biometric-data hub 120. Additionally or alternatively, the biometric sensing devices 110 may be configured to encrypt biometric readings of people not associated with the mobile biometric-data hub 120 and communicate the biometric readings of the user 102 (e.g., because the user 102 is associated with the mobile biometric-data hub 120) in an unencrypted format.

In some embodiments, the mobile biometric-data hub 120 may be configured to authenticate itself as being associated with the particular person. Additionally or alternatively, the mobile biometric data hub 120 may be configured to receive one or more biometric readings from one or more sensors (e.g., the biometric sensing devices 110) and validate that the biometric readings are of the user 102. Additionally or alternatively, the mobile biometric-data hub 120 may be configured to communicate the validated biometric readings to the network-attached device 130.

In some embodiments, the mobile biometric-data hub 120 may be configured to authenticate itself (e.g., by verifying that the mobile biometric data hub 120 is being worn by the particular person). Additionally or alternatively, the mobile biometric data hub 120 may be configured to associate itself with the user 102. For example, the mobile biometric data hub 120 may be configured to obtain a biometric reading and determine whether the biometric reading is similar to a biometric signature of the particular person.

In some embodiments, the mobile biometric data hub 120 may be configured to obtain a biometric signature of the particular person. In some embodiments, the mobile biometric data hub 120 may obtain a biometric reading of a user and define the biometric reading as the biometric signature of the user, such as when the user first puts on the mobile biometric data hub 120. Additionally or alternatively, the mobile biometric data hub 120 may identify the user as the particular person, which may include generating an identifier for the particular person. In some embodiments, the mobile biometric data hub 120 may obtain the biometric signature from another source, for example, the computing device 150.

In some embodiments, the mobile biometric-data hub 120 may include a biometric sensor (such as a heartbeat sensor, a sound sensor, or a sweat sensor, etc.). The mobile biometric data hub 120 may use the included biometric sensor to facilitate the determination that the user 102 is the particular person and to associate the mobile biometric-data hub 120 with the user 102. For example, the mobile biometric-data hub 120 may include a sound sensor. The mobile biometric-data hub 120 may be configured to obtain sound readings, (e.g., from the user 102 speaking or from a heartbeat rhythm of the user 102) and compare the sound readings to a sound signature of the particular person stored in the mobile biometric-data hub 120. If the sound readings are similar enough to the sound signature, the mobile biometric-data hub 120 may authenticate itself as being worn by the particular person and/or associate the mobile biometric-data hub 120 with the user 102.

As another example, the mobile biometric-data hub 120 may touch skin of the user 102 and may include a biometric sensor configured to take biometric readings from skin of the user 102. Continuing the example, the mobile biometric-data hub 120 may include a sweat sensor or sweat vapor sensor. In these or other embodiments, the mobile biometric-data hub 120 may be configured to verify that the mobile biometric-data hub 120 is associated with (e.g., being worn by) the particular person by taking sweat measurements and comparing the sweat measurements to a signature (e.g., a chemical signature) of the particular person.

In some embodiments, the mobile biometric-data hub 120 may be configured to authenticate itself based on biometric readings obtained from one of the biometric sensing devices 110 (e.g., that is separate from the mobile biometric data hub 120). For example, a first biometric sensing device 110A may include a wrist-borne pulse sensing device. The first biometric sensing device 110A may take pulse readings of the user 102 and communicate the pulse readings to the mobile biometric-data hub 120. The mobile biometric-data hub 120 may compare the pulse readings to a biometric pulse signature of the particular person and, based Son a similarity between the pulse readings and the biometric pulse signature, the mobile biometric-data hub 120 may determine that the user 102 is the particular person. Additionally or alternatively, the mobile biometric data hub 120 may associate itself with the first biometric sensing device 110A (e.g., based on receiving the biometric readings from the first biometric sensing device 110A or based on distance between the first biometric sensing device 110A and the mobile biometric data hub 120). Based on the determination that the user 102 is the particular person for which the biometric signature was generated, and based on the association between the mobile biometric data hub 120 and the first biometric sensing device 110A, the mobile biometric data hub 120 may be configured to authenticate the mobile biometric-data hub 120 as being worn by the user 102 (e.g., validate that the user 102 of the mobile biometric data hub 120 is the particular person for which the signature was generated).

In these or other embodiments, the mobile biometric-data hub 120 may be configured to regularly re-authenticate itself and/or re-associate the mobile biometric-data hub 120 with the user 102. For example, the mobile biometric data hub 120 may be configured to authenticate itself in response to the mobile biometric data hub 120 receiving a biometric reading from one of the biometric sensing devices 110. As another example, the mobile biometric-data hub 120 may be configured to cause the authentication of the mobile biometric data hub 120, and/or the association between the mobile biometric-data hub 120 and the user 102 to age or expire after a period of time. In these or other embodiments, the mobile biometric-data hub 120 may be configured to send a communication to one or more biometric sensing devices 110 requesting a biometric reading with which the mobile biometric-data hub 120 can verify that it is still associated with the particular person.

Additionally or alternatively, associating the mobile biometric-data hub 120 with the user 102 may include determining a confidence score indicative of a likelihood that the biometric reading is of the particular person. For example, the mobile biometric-data hub 120 may be configured to determine a similarity between the signature and the biometric reading and generate a confidence score based on the similarity. In some embodiments, the mobile biometric-data hub 120 may be configured to update a pre-existing confidence score based on a recently-calculated confidence score.

In some embodiments, the mobile biometric-data hub 120 may be configured to receive biometric readings from separate biometric sensing devices 110, and validate that the biometric readings are of the user 102 (e.g., of the particular person). For example, the mobile biometric-data hub 120 may be associated with the user 102 based on a first biometric reading from a first biometric sensing device 110A. At another time, the mobile biometric-data hub 120 may receive a second biometric reading from a second biometric sensing device 110B. Based on the association between the mobile biometric-data hub 120 and the user 102 and based on a determination that the second biometric reading is of the user 102 (examples of which are described below), the mobile biometric-data hub 120 may tag the second biometric reading with an identifier associating the second biometric reading with the user 102.

In some embodiments, the mobile biometric-data hub 120 may be configured to determine that the biometric readings are of the user 102 based on a proximity factor. For example, the mobile biometric-data hub 120 may be configured to determine that the second biometric reading from the second biometric sensing devices 110B are of the user 102 based on the mobile biometric-data hub 120 being within a threshold distance from the second biometric sensing device 110B at the time the second biometric reading was taken. Additionally or alternatively, the mobile biometric-data hub 120 may be configured to determine that the second biometric reading from the second biometric sensing devices 110B are of the user 102 based on similarity with previous biometric readings for the user 102. For example, the second biometric reading may be compared to a prior biometric reading or a signature.

As an example of validating biometric data, the mobile biometric-data hub 120 may obtain a biometric reading from the second biometric sensing device 110B, e.g., a blood-pressure reading. The mobile biometric-data hub 120 may determine that the blood-pressure reading is from the user 102 based on the mobile biometric-data hub 120 being within a threshold distance from the second biometric sensing device 110B when the blood-pressure reading is taken.

In some embodiments, the biometric sensing devices 110 and/or the mobile biometric-data hub 120 may be configured to measure distance or detect whether the biometric sensing devices 110 and the mobile biometric-data hub 120 are within the threshold distance. For example, the communication interfaces of the biometric sensing devices 110 and the mobile biometric-data hub 120 may be configured to detect signal strength of communications or signals sent between the biometric sensing devices 110 and the mobile biometric-data hub 120. Additionally or alternatively, the mobile biometric-data hub 120 may compare the blood-pressure reading with a prior blood-pressure reading to determine whether the blood-pressure reading is of the user 102. For example, by determining whether the blood-pressure reading is within a threshold range of the prior blood-pressure reading. For example, threshold ranges for variability of biometric readings may exist. For example, a threshold may indicate that the weight of a user may not change by more than five pounds in a day.

In some embodiments, the mobile biometric-data hub 120 may be configured to tag the second biometric reading with an identifier of the user, e.g., an identification number. Additionally or alternatively, in embodiments in which the mobile biometric-data hub 120 determines a confidence score indicating a likelihood that the user 102 is associated with the mobile biometric-data hub 120, the mobile biometric-data hub 120 may be configured to tag the second biometric reading with the confidence score.

In some embodiments, the mobile biometric-data hub 120 may be configured to communicate the identifier of the user to the biometric sensing devices 110. For example, when the second biometric sensing device 110B communicates the second biometric reading to the mobile biometric-data hub 120, the mobile biometric-data hub 120 may determine that the second biometric reading is associated with the user 102 and communicate the identifier of the user 102 to the second biometric sensing device 110B. Thereafter the second biometric sensing device 110B may be configured to store and communicate the identifier with the second biometric reading e.g., to another mobile biometric-data hub.

In some embodiments, the mobile biometric-data hub 120 may be configured to store the tagged biometric readings while the mobile biometric-data hub 120 is not communicatively coupled to the network-attached device 130 and/or communicate the tagged biometric readings while the mobile biometric-data hub 120 is communicatively coupled to the network-attached device 130. In these and other embodiments, when receiving a biometric reading, the mobile biometric-data hub 120 may be configured to determine whether the mobile biometric-data hub 120 is communicatively coupled to the network-attached device 130. In response the mobile biometric-data hub 120 not being communicatively coupled to the network-attached device 130, the mobile biometric-data hub 120 may store the tagged biometric readings. In response to the mobile biometric-data hub 120 being communicatively coupled to the network-attached device 130, the mobile biometric-data hub 120 may communicate (e.g., wirelessly transmit) the tagged second biometric reading to the network-attached device 130.

Additionally or alternatively, the mobile biometric-data hub 120 may be configured to store and/or communicate biometric readings of other people from the biometric sensing devices 110 to the network-attached device 130. For example, in some embodiments the biometric sensing devices 110 may be configured to take, store, and communicate biometric readings of people that are not associated with the mobile biometric-data hub 120 to the mobile biometric-data hub 120. The mobile biometric-data hub 120 may be configured to receive the biometric readings of the other people and store and/or communicate the biometric readings of the other people to the network-attached device 130.

In some embodiments, the mobile biometric-data hub 120 may be wearable or may be included in a wearable device. For example, the mobile biometric-data hub 120 may be adhered to skin of the user 102, for example, on the chest of the user. As another example, the mobile biometric-data hub 120 may be borne in a pocket of the user 102. As another example, the mobile biometric-data hub 120 may be worn strapped to the user 102, for example, strapped across the chest or arm of the user. In some embodiments, the mobile biometric-data hub 120 may be battery-powered.

In some embodiments, the network-attached device 130 may be configured to receive biometric readings from the mobile biometric-data hub 120 and communicate the biometric readings to the computing device 150, via the network 140. The network-attached device 130 may include one or more communication interfaces, for example, a first communication interface configured to communicate with the mobile biometric-data hub 120 and a second communication interface configured to communicate across the network 140. The first communication interface may be configured to communicate via short-range communication protocols, for example, near-field communications (NFC), wireless 802.11, and/or Bluetooth. The second communication interface may be configured to communicate across the network 140 using, for example, internet protocols such as, for example, Internet Protocol version 4 (IPv4) or Internet Protocol version 6 (IPv6).

In some embodiments, the network-attached device 130 may include a processor and a data storage. The network-attached device 130 may be configured to store biometric readings, for example, buffering the biometric readings for communication to the computing device 150.

In some embodiments, the network-attached device 130 may be configured to send a confirmation to the mobile biometric-data hub 120 indicating that the network-attached device 130 has received the biometric readings.

As an example of the operation of the network-attached device 130 in the environment 100, the network-attached device 130 may be immobile (e.g., plugged into a wall outlet in a home of the user 102). The user 102 may carry the mobile biometric-data hub 120 around throughout the day. Multiple biometric readings may be taken of the user 102 by the multiple biometric sensing devices 110, which may be inside or outside the home of the user 102. The biometric sensing devices 110 may communicate the biometric readings to the mobile biometric-data hub 120. The mobile biometric-data hub 120 may store the biometric readings. When the mobile biometric-data hub 120 is communicatively coupled to the network-attached device 130 (for example, when the user 102 returns home), the mobile biometric-data hub 120 may communicate the biometric readings to the network-attached device 130. The network-attached device 130 may communicate the biometric readings to the computing device 150 via the network 140.

An example of a physical implementation of the biometric sensing devices 110, the mobile biometric data hub 120, and the network-attached device 130 and/or the components of the biometric sensing devices 110, the mobile biometric data hub 120, and the network-attached device 130 are given below with regard to the computing system 200 of FIG. 2. Additional details regarding interactions between the biometric sensing devices 110, the mobile biometric data hub 120, and the network-attached device 130 and the environment 100 are given below with regard to the sequence diagram of FIG. 3.

In some embodiments, the network 140 may include hardware and software configured to communicatively couple computing systems. The network 140 may include any suitable hardware and/or software for communicatively coupling computing systems, for example, a local area network (LAN), a wide area network (WAN), a cellular radio frequency (RF) network, and/or the Internet.

In some embodiments, the computing device 150 may include any suitable computing device attached to the network 140. The computing device 150 may include a web server or a data server. The computing device 150 may be configured to store biometric readings. Additionally or alternatively, the computing device 150 may be configured to analyze biometric readings. In some embodiments, the computing device 150 may be configured to present, or allow access to the biometric readings.

In some embodiments, the third party 160 may include a third party that may desire to view the biometric readings or information about the biometric readings. The third party 160 may include a healthcare professional of the user 102, or another interested party, for example, an insurance company, a professional agent, a personal trainer, etc. In some embodiments, the user 102 may access the biometric data stored at the computing device 150.

In some embodiments, the third party 160 may be able to access biometric data (e.g., biometric readings or information derived from biometric readings) of the user 102 stored at the computing device 150. The third party 160 may access the biometric data via a communication network (not shown) e.g., the Internet. In some embodiments, the computing device 150 may be configured to allow access to the biometric data through an interface, such as an Application Programming Interface (API).

In some embodiments, the environment 100 may operate to validate biometric readings and communicate the biometric readings to the computing device 150 with little or no active involvement from the user 102. For example, the mobile biometric data hub 120 may authenticate itself and validate the biometric readings of the biometric sensing devices 110 without the user 102 providing specific instructions to the mobile biometric data hub 120 and/or the biometric sensing devices 110. Additionally or alternatively, the mobile biometric data hub 120 may be configured to communicate the validated biometric readings to the network-attached device 130 without the user 102 providing interaction except being near the network-attached device 130. Additionally or alternatively, the network-attached device 130 may be configured to transmit the validated biometric readings to the computing device 150 without involvement from the user 102.

To decrease required involvement of the user 102 in the operations of the environment 100, elements of the environment 100 may be configured to communicate without direction or instruction from the user 102. For example, the biometric sensing devices 110 may be configured to wirelessly transmit biometric readings as they are taken, and for a duration of time afterward, and/or a number of times afterward. Additionally or alternatively, the mobile biometric data hub 120 may be configured to continually listen for transmissions from biometric sensing devices 110.

In some embodiments, the biometric sensing devices 110 may be programmed such that upon taking a reading, the biometric sensing devices 110 either listen for a pairing signal or transmit a pairing signal. Additionally or alternatively, the mobile biometric data hub 120 may be programmed to periodically listen for a pairing signal or periodically transmit a pairing signal. In these and other embodiments, without input from the user 102, the mobile biometric data hub 120 and one or more of the biometric sensing devices 110 may be paired such that biometric readings from the biometric sensing devices 110 may be communicated to the mobile biometric data hub 120 over a secure communication channel established between them.

In some embodiments, the mobile biometric data hub 120 may be configured to broadcast the identifier of the user 102 continually, at regular intervals, or in response to receiving a biometric reading and/or in response to verifying that a received biometric reading is of the user 102. Additionally or alternatively, the mobile biometric data hub 120 may be configured to ping, e.g., at regular intervals, to determine whether it can communicate with the network-attached device 130. Additionally or alternatively, the network-attached device 130 may be configured to broadcast a signal indicating its availability for connection to a mobile biometric data hub 120, such that when a mobile biometric data hub 120 receives the signal, the mobile biometric data hub 120 may reply with biometric readings and/or a transmission to establish a communicative coupling between the mobile biometric data hub 120 and the network-attached device 130.

In some embodiments, some of the various communications between the elements of the environment 100 may include establishing a connection between the elements e.g. pairing. In some embodiments, the various elements of the environment 100 may be configured to connect automatically. Additionally or alternatively, in some embodiments, some aspects of the established connection may be predefined. For example, a blood-pressure sensing device may be sold with a mobile biometric data hub 120, and at the time the blood-pressure sensing device and the mobile biometric data hub 120 are sold, there may be a predefined connection between the blood-pressure sensing device and the mobile biometric data hub 120. Additionally or alternatively, a third party may manually pair the mobile biometric data hub 120 and/or one or more of the biometric sensing devices 110 and/or network-attached devices 130.

Modifications, additions, or omissions may be made to the environment 100 without departing from the scope of the present disclosure. For example, in some embodiments the environment 100 may include any number of biometric sensing devices 110, for example, one, or ten. Additionally or alternatively, one or more of the biometric sensing devices 110 may be worn or borne by the user 102. Additionally or alternatively, the user 102 may access the biometric data of the user 102 stored on the computing device 150. Further, the order of operations may vary according to different implementations.

Figure 2:
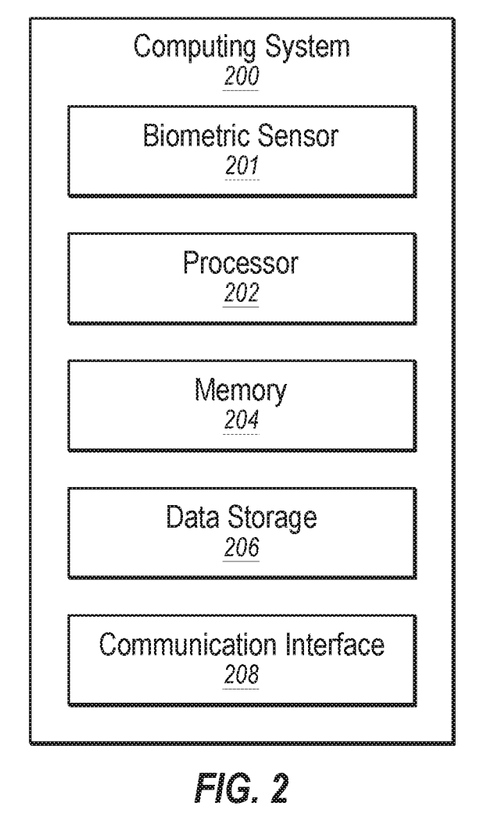
FIG. 2 illustrates various example implementations of a biometric sensing device, a mobile biometric-data hub, a network-attached device, or a computing device in the environment of FIG. 1.

FIG. 2 is a block diagram of an example computing system 200, which may be according to at least one embodiment described in the present disclosure. Any or all of the biometric sensing devices 110, the mobile biometric-data hub 120, the network-attached device 130, and the computing device 150 of FIG. 1 may include the computing system 200. Additionally or alternatively, any or all of the biometric sensing devices 110, the mobile biometric-data hub 120, the network-attached device 130, and the computing device 150 of FIG. 1 may include a subset of the components of the computing system 200. As illustrated in FIG. 2, the computing system 200 may include a biometric sensor 201 a processor 202, a memory 204, a data storage 206, and a communication interface 208.

Generally the biometric sensor 201 may include any suitable sensor configured to take a reading of a user, for example, a temperature sensor (e.g., a thermometer), a light sensor (e.g., to take a heart-rate reading), a chemical sensor (e.g., to measure chemicals in sweat, sweat vapor, blood, or saliva), an accelerometer (e.g., for gait analysis), a gyroscope, a sound sensor (e.g., to measure sound, including a voice or heartbeat of a user), an electrical sensor (e.g., to measure galvanic skin response), or a weight sensor (e.g., a scale), among others.

Generally, the processor 202 may include any suitable special-purpose or general-purpose computer, computing entity, or processing device including various computer hardware or software modules and may be configured to execute instructions stored on any applicable computer-readable storage media. For example, the processor 202 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 2, it is understood that the processor 202 may include any number of processors distributed across any number of network or physical locations that are configured to perform individually or collectively any number of operations described herein. In some embodiments, the processor 202 may interpret and/or execute program instructions and/or process data stored in the memory 204, the data storage 206, or the memory 204 and the data storage 206. In some embodiments, the processor 202 may fetch program instructions from the data storage 206 and load the program instructions in the memory 204. After the program instructions are loaded into the memory 204, the processor 202 may execute the program instructions, such as instructions to perform one or more operations described with respect to the biometric sensing devices 110, the mobile biometric-data hub 120, the network-attached device 130, and the computing device 150 of FIG. 1.

For example, a processor 202 in a mobile biometric data hub 120 may be configured to execute instructions to perform operations including authenticating the mobile biometric data hub 120, validate biometric readings of the biometric sensing devices 110, and instructing the communication interface 208 to communicate the validated readings. As another example, a processor 202 in a first biometric sensing device 110A may be configured to execute instructions to perform operations including determining when to store and/or communicate biometric readings and encrypting biometric readings.

The memory 204 and the data storage 206 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 202. By way of example, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 202 to perform a certain operation or group of operations. In these and other embodiments, the term "non-transitory" as explained herein should be construed to exclude only those types of transitory media that were found to fall outside the scope of patentable subject matter in the Federal Circuit decision of *In re Nuijten,* 500 F.3d 1346 (Fed. Cir. 2007). Combinations of the above may also be included within the scope of computer-readable media.

The communication interface 208 may be configured to communicate biometric readings and to and from the data storage 206. The communication interface 208 may include any device, system, component, or collection of components configured to allow or facilitate communication between the computing system 200 and a network and/or other computing systems 200. For example, the communication interface 208 may include, a modem, a network card (wireless or wired), an infrared communication device, an optical communication device, a wireless communication device (such as an antenna), and/or chipset (such as a Bluetooth device, an 802.6 device (e.g., Metropolitan Area Network (MAN)), a Wi-Fi device, a WiMAX device, cellular communication facilities, etc.), and/or the like. The communication interface 208 may permit data to be exchanged with any network such as a cellular network, a Wi-Fi network, a MAN, an optical network, etc., to name a few examples, and/or any other devices described in the present disclosure, including remote devices.

Modifications, additions, or omissions may be made to the computing system 200 without departing from the scope of the present disclosure. For example, the data storage 206 may be located in multiple locations and accessed by the processor 202 through a network.

As an example of an implementation of a biometric sensing device 110 of FIG. 1, a first biometric sensing device 110A may include the biometric sensor 201, and the communication interface 208 (e.g., omitting the processor 202, the memory 204, and the data storage 206). In these or other embodiments, the first biometric sensing device 110A may be configured to take biometric readings and communicate the biometric readings to the mobile biometric-data hub 120 of FIG. 1. In other embodiments, the first biometric sensing device 110A may include the processor 202, the memory 204 and the data storage 206. In these embodiments, the first biometric sensing device 110A may be configured to store biometric readings in the data storage 206. Additionally or alternatively, the first biometric sensing device 110A may be configured to determine when and/or how to communicate the biometric readings to the mobile biometric-data hub 120. Additionally or alternatively, the first biometric sensing device 110A may be configured to use the processor 202 to encrypt one or more biometric readings prior to storing or communicating the biometric readings to the mobile biometric-data hub 120.

As an example of an implementation of a mobile biometric-data hub 120 of FIG. 1, the mobile biometric-data hub 120 may include the biometric sensor 201, the processor 202, the memory 204, the data storage 206, and the communication interface 208. The mobile biometric-data hub 120 may be configured to obtain first biometric readings from the biometric sensor 201 and receive second biometric readings via the communication interface 208. The mobile biometric data hub 120 may be configured to determine whether the mobile biometric-data hub 120 is associated with the user based on the first biometric readings, and determine if the second biometric readings are associated with the user using the processor 202. The mobile biometric-data hub 120 may be configured to store the biometric readings at the data storage 206 and communicate the biometric readings via the communication interface 208. In some embodiments, the mobile biometric-data hub 120 may not include the biometric sensor 201, in which case the first biometric readings used to authenticate the mobile biometric data hub 120 as being associated with the user may be received via the communication interface 208.

In some embodiments, the mobile biometric data hub 120 may include a single communication interface 208 configured to communicate with both the biometric sensing devices 110 and the network-attached device 130. In some embodiments, the mobile biometric-data hub 120 may include two communication interfaces 208, for example, one for communicating with the biometric sensing devices 110 and one for communicating with the network-attached device 130 of FIG. 1. For example, the mobile biometric-data hub 120 may include a first communication interface 208 configured for short-range wireless communications (e.g., using a protocol such as Bluetooth®) configured for communication with one or more of the biometric sensing devices 110. Additionally or alternatively, the mobile biometric-data hub 120 may include a second communication interface 208 (e.g., using a protocol such as wireless 802.11) configured for communication with the network-attached device 130.

As an example of an implementation of the network-attached device 130, the network-attached device 130 may include the processor 202, the memory 204, the data storage 206, and the communication interface 208, and may exclude the biometric sensor 201. An example implementation of the computing device 150 of FIG. 1 may include the processor 202, the memory 204, the data storage 206, and the communication interface 208, and may exclude the biometric sensor 201.

Figure 3:
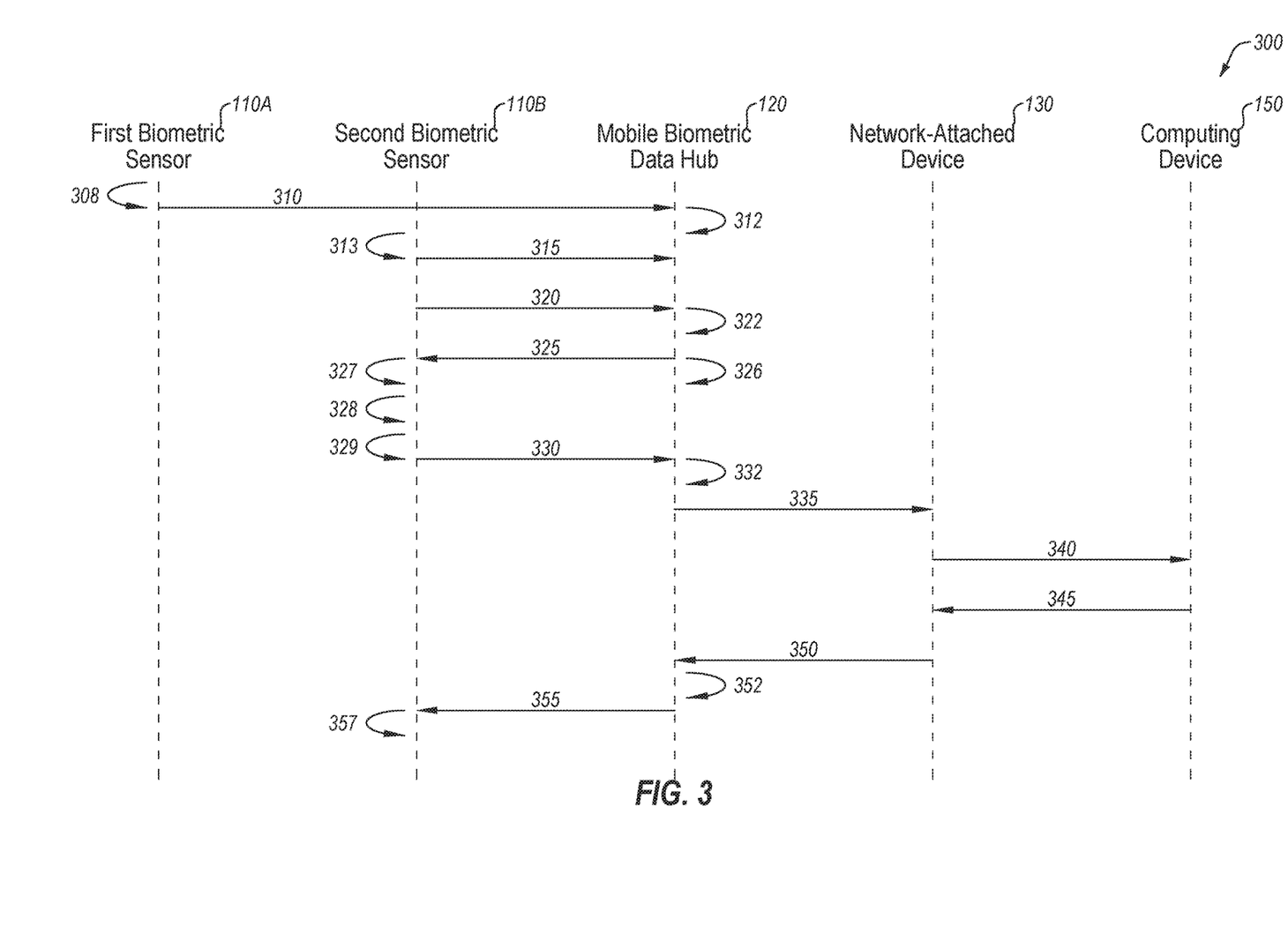
FIG. 3 is a sequence diagram of messages, events, and/or operations that may be included in or performed by at least one embodiment described in the present disclosure.

FIG. 3 is a sequence diagram of messages, events, and/or operations that may be included in or performed by at least one embodiment described in the present disclosure. For example, a sequence 300 may include messages, events, and/or operations of a first biometric sensing device 110A, a second biometric sensing device 110B, a mobile biometric-data hub 120, a network-attached device 130, and a computing device 150, all as described above in regard to FIGS. 1 and 2. While described as a "sequence," it will be appreciated that the messages, events, and/or operations may occur in a different order than illustrated, may be omitted, and/or may be performed simultaneously.

The sequence 300 may begin at a first event 308. The first event may include the first biometric sensing device 110A taking a first biometric reading of a user.

The sequence 300 may continue with a first message 310 in which the first biometric sensing device 110A may communicate the first biometric reading to the mobile biometric-data hub 120. In some embodiments, the first message 310 may be sent via wireless communication. In some embodiments, the first biometric sensing device 110A may be included in or connected to (e.g., via a wire) the mobile biometric-data hub 120 such that the first message 310 may be omitted or communicated across a wire, bus, or other electrical connection.

The sequence 300 may continue with a first operation 312. The first operation 312 may include the mobile biometric-data hub 120 authenticating itself, and/or associating the mobile biometric-data hub 120 with the user. For example, in response to the mobile biometric-data hub 120 receiving the first message 310, including the first biometric reading, the mobile biometric-data hub 120 may be configured to verify that the first biometric reading is of the user (e.g., that the first biometric reading is of the particular person). The first operation 312 may include comparing the first biometric reading to a signature biometric reading. Based on the first biometric reading being of the user and based on an association between the first biometric sensor 110A and the mobile biometric data hub 120, the mobile biometric data hub 120 may be configured to authenticate the mobile biometric data hub 120. Additionally or alternatively, the mobile biometric data hub 120 may be configured to associate the mobile biometric data hub 120 with the user.

In some embodiments, one or more additional messages may be sent between the first biometric sensing device 110A and the mobile biometric-data hub 120 such that the first biometric sensing device 110A may be associated with the mobile biometric-data hub 120. The association between the first biometric sensing device 110A and the mobile biometric-data hub 120 may be such that when the first biometric reading is verified as being associated with the user, the mobile biometric-data hub 120 may be authenticated and/or associated with the user by virtue of the first biometric sensing device 110A being associated with the mobile biometric-data hub 120. These additional messages may be beneficial in embodiments in which the first biometric sensing device 110A is not included in or directly connected to the mobile biometric-data hub 120. The additional messages may include messages and/or transmissions allowing for a determination of distance between the first biometric sensing device 110A and the mobile biometric data hub 120, and/or a determination whether the first biometric sensing device 110A is within a threshold distance from the mobile biometric data hub 120. In some embodiments, the additional message may be repeated regularly.

The sequence 300 may include a second event 313. The second event may include the second biometric sensing device 110B taking a second biometric reading of the user. The second event 313 may take place at any time, for example, before the first event 308, the first message 310, and/or the first operation 312.

The sequence 300 may continue with a second message 315 in which the second biometric sensing device 110B may communicate the second biometric reading to the mobile biometric-data hub 120. In some embodiments, the second message 315 may be sent based on the second biometric sensing device 110B and the mobile biometric-data hub 120 being paired and being within communicative range of each other. Additionally or alternatively, the second message 315 may be sent based on a pairing sequence between the second biometric sensing device 110B and the mobile biometric-data hub 120.

The sequence 300 may continue with a third message 320 in which the second biometric sensing device 110B may transmit a signal to the mobile biometric-data hub 120. The mobile biometric-data hub 120 may be configured to determine that the second biometric sensing device 110B is within a threshold distance from the mobile biometric-data hub 120 based on the signal. In some embodiments, the third message may be omitted and the mobile biometric-data hub 120 may be configured to determine whether the second biometric sensing device 110B is within the threshold distance from the mobile biometric-data hub 120 based on the second message 315, for example, based on the received signal strength of the second message 315.

The sequence 300 may continue with a second operation 322. At the second operation 322, the mobile biometric-data hub 120 may verify that the second biometric reading is of the user and/or associate the second biometric reading with the user. For example, based on the association between the mobile biometric-data hub 120 and the user, and based on the second biometric reading being of the user, the mobile biometric-data hub 120 may be configured to tag the second biometric reading with an identifier of the user. The association between the mobile biometric-data hub 120 and the user may have been established during the first operation 312.

The second operation 322 may additionally or alternatively include determining that the second biometric reading is of the user. Determining that the second biometric reading is of the user may be based on a determination that the second biometric sensing device 110B was within a threshold distance from the mobile biometric-data hub 120 when the second biometric measurement was taken. Additionally or alternatively, determining that the second biometric reading is of the user may be based on a comparison between the second biometric reading and a prior biometric reading of the user. Tagging the second biometric reading with an identifier of the user may include associating the identifier of the user with the second biometric reading in the data storage of the mobile biometric-data hub 120.

The sequence 300 may continue with a fourth message 325 in which the mobile biometric-data hub 120 may communicate a confirmation of the association between the second biometric reading and the user to the second biometric sensing device 110B. In some embodiments, the fourth message 325 may include the identifier of the user.

The sequence 300 may continue with a third operation 326. At the third operation 326, the mobile biometric-data hub 120 may store the second biometric reading, including the identifier of the user in data storage of the mobile biometric-data hub 120.

The sequence 300 may continue with a fourth operation 327. At the fourth operation 327, the second biometric sensing device 110B may store the second biometric reading, which may include the identifier of the user or some other indication that the second biometric reading has been validated and/or associated with the user. The second biometric sensing device 110B may be configured to store the tagged second biometric reading in order to, at a later time, communicate the tagged second biometric reading to another mobile biometric-data hub. The second biometric sensing device 110B may be configured to encrypt the tagged second biometric reading before storing and/or communicating the tagged second biometric reading. In this way, the second biometric sensing device 110B may be configured to preserve the privacy of the user when communicating the tagged second biometric reading to the other mobile biometric-data hub.

The sequence 300 may include a third event 328 at any time during the sequence 300. The third event 328 may precede any or all of the above-described events, operations and messages. At the third event 328, the second biometric sensing device 110B may obtain a third biometric reading of a second person, e.g., a person other than the user.

The third event 328 may be followed by a fifth operation 329. At the fifth operation 329, the second biometric sensing device 110B may store the third biometric reading. In some embodiments, the second biometric sensing device 110B may be configured to encrypt the third biometric reading before or during storing the third biometric reading.

The fifth operation 329 may be followed by a fifth message 330 in which the second biometric sensing device 110B may communicate the third biometric reading to the mobile biometric-data hub 120. In some embodiments, the third biometric reading may be encrypted. In this way, the privacy of the second person may be preserved when the third biometric reading is communicated to the mobile biometric-data hub 120.

The fifth message 330 may be followed by a sixth operation 332. At the sixth operation 332, the mobile biometric-data hub 120 may be configured to store the third biometric reading.

In some embodiments, following the second operation 322, and/or the reception of the fifth message 330, the mobile biometric-data hub 120 may determine whether it is communicatively coupled to the network-attached device 130. If the mobile biometric-data hub 120 is communicatively coupled to the network-attached device 130, the mobile biometric-data hub 120 may communicate the tagged second biometric reading and/or the third biometric reading to the network-attached device 130, for example through a sixth message 335. If the mobile biometric-data hub 120 is not communicatively coupled to the network-attached device 130, the mobile biometric-data hub 120 may store the tagged second biometric reading and/or the third biometric reading, for example, at the third operation 326 and/or the sixth operation 332.

The sequence 300 may continue with the sixth message 335 in which the mobile biometric-data hub 120 communicates to the network-attached device 130 the tagged second biometric reading and/or the third biometric reading. Such communication may include a batch communication that includes all stored or a subset of all stored biometric readings. Additionally or alternatively the biometric readings may be communicated individually.

The sequence 300 may continue with the seventh message 340 in which the network-attached device 130 may communicate the tagged second biometric reading and/or the third biometric reading to the computing device 150 over a communication network (e.g., the network 140 of FIG. 1). Additionally or alternatively, the network-attached device 130 may store the tagged second biometric reading and/or the third biometric reading, for example, until a confirmation has been received indicating that the communication of the seventh message 340 was successfully received.)

The sequence 300 may continue with an eighth message 345 in which the computing device 150 may communicate confirmation of the reception of the tagged second biometric reading and/or the third biometric reading to the network-attached device 130.

The sequence 300 may continue with a ninth message 350 from the network-attached device 130 to the mobile biometric-data hub 120. The ninth message 350 may include a confirmation of the reception of the tagged second biometric reading and/or the third biometric reading by the network-attached device 130. In some embodiments, the ninth message 350 may be in response to the sixth message 335, (e.g., without regard for communications with the computing device 150). In these embodiments, the ninth message 350 may indicate that the tagged second biometric reading and/or the third biometric reading were successfully received by the network-attached device 130. Additionally or alternatively, the ninth message 350 may be in response to the eighth message 345. In these embodiments the ninth message 350 may, additionally or alternatively, indicate that the tagged second biometric reading and/or the third biometric reading were successfully received by the computing device 150.

The sequence 300 may continue with a seventh operation 352. At the seventh operation 352, the mobile biometric-data hub 120 may delete the tagged second biometric reading and/or the third biometric reading from the data storage of the mobile biometric-data hub 120. In some embodiments, the mobile biometric-data hub 120 may be configured to not delete the tagged second biometric reading and/or the third biometric reading until the mobile biometric-data hub 120 has received a confirmation that the network-attached device 130 (and/or the computing device 150) has successfully received the tagged second biometric reading and/or the third biometric reading (e.g., through the ninth message 350). In these and other embodiments, the deletion may be in response to the confirmation that the network-attached device 130 and/or the computing device 150 has successfully received the biometric readings.

The sequence 300 may continue with a tenth message 355 in which the mobile biometric-data hub 120 communicates, to the second biometric sensing device 110B, a confirmation indicating that the network-attached device 130 (and/or the computing device 150) successfully received the tagged second biometric reading and/or the third biometric reading.

The sequence 300 may continue with an eighth operation 357. At the eighth operation 357, the second biometric sensing device 110B may delete the tagged second biometric reading and/or the third biometric reading from the data storage of the second biometric sensing device 110B. In some embodiments, the second biometric sensing device 110B may be configured to not delete the tagged second biometric reading and/or the third biometric reading until the second biometric sensing device 110B has received a confirmation that the network-attached device 130 (and/or the computing device 150) has successfully received the tagged second biometric reading and/or the third biometric reading (e.g., through the tenth message 355).

Modifications, additions, or omissions may be made to the sequence 300 without departing from the scope of the present disclosure. For example, in some embodiments, the third message 320 may be omitted. Additionally or alternatively, in some embodiments, the third operation 326, and/or the sixth operation 332 may be omitted. Further, the order of operations may vary according to different implementations. For example, the tenth message 355 may precede the seventh operation 352. As another example, the third event 328, the fifth operation 329, and the fifth message 330 may precede any or all of the previously described events, operations and/or messages.

Figure 4:
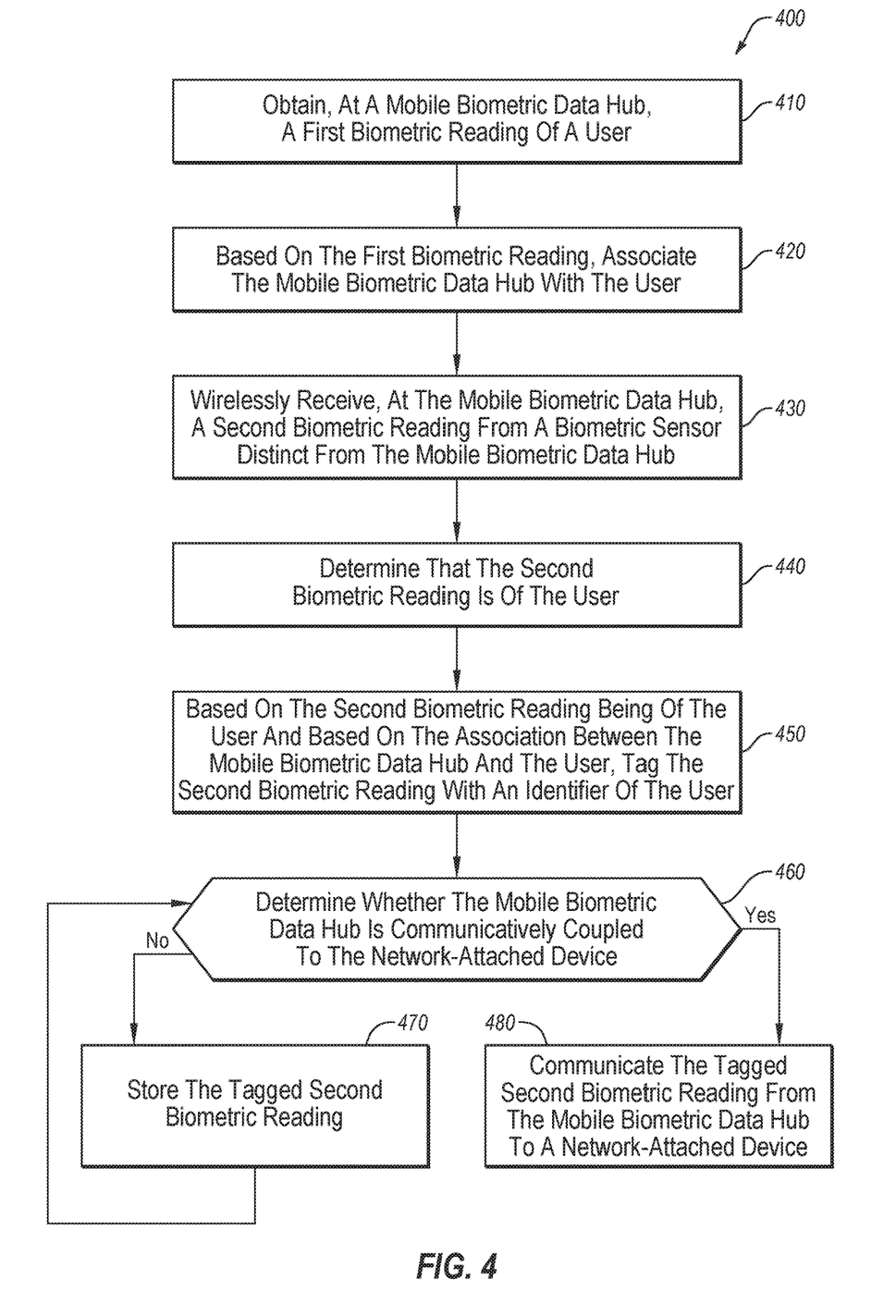
FIG. 4 includes a flow chart of an example method to communicate validated biometric readings, all according to at least one embodiment described in the present disclosure.

FIG. 4 is a flow chart of an example method 400 configured to communicate validated biometric readings, according to at least one embodiment described in the present disclosure. In some embodiments, one or more of the operations associated with the method 400 may be performed by one or more elements of the environment 100 of FIG. 1. For example, the mobile biometric-data hub 120, the biometric sensing devices 110, and/or the network-attached device 130 may perform one or more of the operations associated with the method 400. Additionally or alternatively, the method 400 may be performed by any suitable system, apparatus, or device. Although illustrated with discrete blocks, the steps and operations associated with one or more of the blocks of the method 400 may be divided into additional blocks, combined into fewer blocks, or eliminated, depending on the desired implementation.

At block 410, a first biometric reading of a user may be obtained, at a mobile biometric-data hub. The user 102 of FIG. 1 may be an example of the user. The mobile S biometric-data hub 120 of FIG. 1 may be an example of the mobile biometric-data hub. In some embodiments, the first biometric reading may be taken by the mobile biometric-data hub, for example, by a first biometric sensor included in or attached to the mobile biometric-data hub. In some embodiments, the first biometric reading may be obtained from a first biometric sensing device, for example, the first biometric sensing device 110A of FIG. 1 which may be distinct from the mobile biometric-data hub.

At block 420, the mobile biometric-data hub may be associated with the user based on the first biometric reading. In some embodiments, it may be determined that the first biometric reading is of a particular person (e.g., by comparing the first biometric reading to a biometric signature of the particular person). If the first biometric reading is of the particular person, it may be determined that the user of the mobile biometric-data hub is the particular person. Additionally or alternatively, an association may have been made between the first biometric sensor and the mobile biometric-data hub (e.g., based on the first biometric sensor being included in or attached to the mobile biometric-data hub, or the first biometric sensor being within a threshold distance from the mobile biometric-data hub when the first biometric reading was taken). Based on the association between the first biometric sensor and the mobile biometric-data hub, the mobile biometric-data hub may be configured to associate itself with the particular person. Additionally or alternatively, the mobile biometric-data hub may be configured to authenticate itself as being associated with the particular person.

In some embodiments, to associate the mobile biometric-data hub with the user, the mobile biometric-data hub may compare the first biometric reading with a signature biometric reading and based on a similarity between the first biometric reading and the signature biometric reading, the mobile biometric-data hub may be associated with the user.

In some embodiments, the association between the mobile biometric-data hub and the first biometric reading may include a confidence score. For example, the confidence score may indicate a likelihood that the first biometric reading is of the particular person. The confidence score may be based on the similarity between the first biometric reading and the signature biometric reading. Additionally or alternatively, the confidence score may be based on multiple biometric readings.

At block 430, a second biometric reading from a biometric sensor distinct from the mobile biometric-data hub may be wirelessly received at the mobile biometric-data hub. The biometric sensor distinct from the mobile biometric-data hub may be a second biometric sensor and may be included in a second biometric sensing device, e.g., the second biometric sensing device 110B of FIG. 1. The biometric sensor 201 of the second biometric sensing device 110B may be an example of the second biometric sensor. The second biometric reading may be communicated by a communication interface 208 of the second biometric sensing device and may be received by a communication interface 208 of the mobile biometric-data hub.

At a block 440 it may be determined that the second biometric reading is of the user. In some embodiments, the determination that the second biometric reading is of the user may be based on a determination that the mobile biometric-data hub is within a threshold distance from the second biometric sensor when the second biometric reading is taken. For example, the mobile biometric-data hub may be configured to measure a received signal strength of a transmission from the second biometric sensor (or the second biometric sensing device that includes the biometric sensor). The mobile biometric-data hub may be configured to determine whether the mobile biometric-data hub is within the threshold distance from the second biometric sensor based on the received signal strength. In some embodiments, the transmission may be the communication of the second biometric reading from the second biometric sensor (or a communication interfaced attached thereto) to the mobile biometric-data hub. Additionally or alternatively, the determination that the second biometric reading is of the user may be based on a similarity between the second biometric reading and one or more prior biometric readings of the user.

At a block 450, the second biometric reading may be tagged with an identifier of the user. The determination to tag the second biometric reading with the identifier of the user may be based on the determination that the second biometric reading is of the user and the association between the mobile biometric-data hub and the user. Tagging the second biometric reading with the identifier of the user may include associating the second biometric reading with the identifier of the user in memory of at least the mobile biometric-data hub.

In embodiments where the association between the mobile biometric-data hub and the user includes the confidence score, tagging the second biometric reading with the identifier may include tagging the second biometric reading with the confidence score.

In some embodiments, the mobile biometric-data hub may be configured to communicate the identifier to the second biometric sensing device. The communication of the identifier may be in response to the determining that the second biometric reading is associated with the user. In these or other embodiments, the second biometric sensing device may be configured to store the second biometric reading, the identifier, and/or an association between the identifier and the second biometric reading.

At a block 460, it may be determined whether the mobile biometric-data hub is communicatively coupled to the network-attached device. The network-attached device 130 of FIG. 1 may be an example of the network attached device.

At a block 470, in response to the mobile biometric-data hub not being communicatively coupled to the network-attached device, the mobile biometric-data hub may be configured to store the tagged second biometric reading. After the block 470, the method 400 may return to the block 460.

At a block 480, in response to the mobile biometric-data hub being communicatively coupled to the network-attached device, the mobile biometric-data hub may be configured to communicate the tagged second biometric reading from the mobile biometric-data hub to a network-attached device.

In some embodiments, the network-attached device may be configured to communicate the tagged second biometric reading to a separate computing device over a communication network. The computing device 150 of FIG. 1 may be an example of the separate computing device. The network 140 of FIG. 1 may be an example of the communication network.

In some embodiments, the network-attached device may be configured to communicate a confirmation indicating that the network-attached device received the tagged second biometric reading. In these or other embodiments, the mobile biometric-data hub may be configured to store the tagged second biometric reading until the mobile biometric-data hub has received the confirmation. In these or other embodiments, the mobile biometric-data hub may be configured to delete the stored second biometric reading after receiving the confirmation.

In these or other embodiments, the mobile biometric-data hub may be configured to communicate an indication of the confirmation to the second biometric sensing device. In these or other embodiments, the second biometric sensing device may be configured to store the second biometric reading until the second biometric sensing device has received the indication. In these or other embodiments, the second biometric sensing device may be configured to delete the stored second biometric reading after receiving the indication.

In embodiments where the second biometric sensing device is configured to store the second biometric reading and/or the identifier, the second biometric sensing device may be configured to encrypt the second biometric reading. Additionally or alternatively, the second biometric sensing device may be configured to communicate the second biometric reading and/or the identifier to another mobile biometric-data hub of another person, e.g., a person other than the user. The other mobile biometric-data hub of the other person may be configured to store the second biometric device (whether encrypted or not and whether tagged with an identifier or not) and communicate the second biometric reading to the network attached device (or another network-attached device). In instances where the second biometric reading is tagged or associated with an identifier, the second biometric reading may be associated with the user on the separate computing device. Thus, the user, or a third party, may be able to access the second biometric reading, and see the association between the second biometric reading and the user, even if the second biometric reading was not communicated to the separate computing device by the mobile biometric-data hub of the user.

In like manner, the second biometric sensing device may be configured to store a third biometric reading of a second person, e.g., a person that is not the user. The second biometric sensing device may be configured to store an association between the second person and the third biometric reading, e.g., based on a second identifier from a second mobile biometric-data hub of the second person. The second biometric sensing device may be configured to encrypt the third biometric reading. The second biometric sensing device may be configured to communicate the third biometric reading (whether encrypted or not) to the mobile biometric-data hub. The mobile biometric-data hub may be configured to store the third biometric reading and communicate the third biometric reading to the network-attached device. The network-attached device may be configured to communicate the third biometric reading to the separate computing device. If the third biometric reading is associated with the second person, (e.g., associated with the second identifier) the association may be included in the communications such that on the separate computing device, the third biometric reading may be associated with the second person. Thus, the second person, or a third party, may be able to access the third biometric reading in association with the second person even if the second mobile biometric-data hub of the second person did not communicate the third biometric reading to the separate computing device.

Modifications, additions, or omissions may be made to the method 400 without departing from the scope of the present disclosure. Further, the order of operations may vary according to different implementations. For example, the block 430 and the block 440 may occur prior to the block 410 and the block 420.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method comprising:
obtaining, at a mobile biometric-data hub, a first biometric reading of a user;
based on the first biometric reading, associating the mobile biometric-data hub with the user;
wirelessly receiving, at the mobile biometric-data hub, a second biometric reading from a biometric sensor distinct from the mobile biometric-data hub;
determining that the second biometric reading is of the user;
based on the second biometric reading being of the user and based on the association between the mobile biometric-data hub and the user, tagging the second biometric reading with an identifier of the user;
wirelessly receiving, at the mobile biometric-data hub, a third biometric reading sensed previously by the biometric sensor, the third biometric reading tagged with a second identifier of a second user; and
communicating both the tagged second biometric reading from the mobile biometric-data hub and the third biometric reading tagged with the second identifier of the second user to a network-attached device in a single batch.

2. The method of claim 1, wherein the determining that the second biometric reading is of the user comprises determining that the mobile biometric-data hub is within a threshold distance from the biometric sensor when the second biometric reading is taken.

3. The method of claim 1, wherein the associating the mobile biometric-data hub with the user comprises determining a confidence score indicative of a likelihood that the first biometric reading is of the user, and wherein tagging the second biometric reading includes tagging the second biometric reading with the confidence score.

4. The method of claim 1, further comprising:
determining whether the mobile biometric-data hub is communicatively coupled to the network-attached device; and
in response to the mobile biometric-data hub not being communicatively coupled to the network-attached device, storing the tagged second biometric reading;
wherein communicating the tagged second biometric reading in response to the mobile biometric-data hub being communicatively coupled to the network-attached device.

5. The method of claim 1, further comprising storing the tagged second biometric reading at the mobile biometric-data hub until the mobile biometric-data hub receives a confirmation from the network-attached device confirming that the network-attached device has received the tagged second biometric reading.

6. A mobile biometric-data hub comprising:
a data storage;
a first biometric sensor configured to take a first biometric reading of a user;
a communication interface configured to:
wirelessly receive a second biometric reading of the user from a second biometric sensor; and
wirelessly receive a third biometric reading sensed previously by the second biometric sensor, the third biometric reading tagged with a second identifier of a second user;
a processor configured to execute instructions to perform operations, the operations comprising:
associate the mobile biometric-data hub with the user based on the first biometric reading;
determine that the second biometric reading is of the user;
based on the second biometric reading being of the user and based on the association between the mobile biometric-data hub and the user, tag the second biometric reading with an identifier of the user;
instruct the data storage to store the second biometric reading and the third biometric reading; and
direct the communication interface to communicate both the tagged second biometric reading and the third biometric reading tagged with the second identifier of the second user to a network-attached device in a single batch.

7. The mobile biometric-data hub of claim 6, wherein the mobile biometric-data hub is configured to be worn on skin of the user and the first biometric sensor touches the skin.

8. The mobile biometric-data hub of claim 6, wherein the communication interface is further configured to measure a received signal strength of a transmission from the second biometric sensor; wherein the operations further comprise determine whether the second biometric sensor is within a threshold distance from the mobile biometric-data hub based on the received signal strength; and wherein the determining that the second biometric reading is of the user is based on the second biometric sensor being within the threshold distance.

9. The mobile biometric-data hub of claim 8, wherein the transmission includes the second biometric reading.

10. A system comprising:
a biometric sensing device comprising:
a first biometric sensor configured to take a first biometric reading of a user;
a storage device configured to store the first biometric reading and a previously sensed second biometric reading tagged with a second identifier of a second user; and
a first communication interface configured to wirelessly transmit the first biometric reading and the previously sensed second biometric reading;
a mobile biometric-data hub comprising:

a second communication interface configured to wirelessly receive the first biometric reading and the second biometric reading;
a processor configured to execute instructions to perform operations, the operations comprising:
determine that the first biometric reading is of the user;
based on the first biometric reading being of the user, tag the first biometric reading with an identifier of the user; and
direct the second communication interface to wirelessly transmit the tagged first biometric reading and the second biometric reading tagged with the second identifier of the second user; and
a data storage configured to store the instructions, the tagged first biometric reading, and the second biometric reading tagged with the second identifier of the second user;
a network-attached device comprising:
a third communication interface configured to wirelessly receive the tagged first biometric reading and the second biometric reading tagged with the second identifier of the second user in a single batch; and
a fourth communication interface configured to communicate the tagged first biometric reading to a separate computing device over a communication network.

11. The system of claim 10, wherein the fourth communication interface is the third communication interface.

12. The system of claim 10, wherein the mobile biometric-data hub further comprises a second biometric sensor configured to take a second biometric reading of the user, wherein the operations further comprise associate the mobile biometric-data hub with the user based on the second biometric reading, and wherein the tagging the first biometric reading is further based on the association between the mobile biometric-data hub and the user.

13. The system of claim 10, wherein the determining that the first biometric reading is of the user comprises determining that the mobile biometric-data hub is within a threshold distance from the biometric sensing device when the first biometric reading is taken.

14. The system of claim 10, wherein the operations further comprise:
determine whether the second communication interface is communicatively coupled to the third communication interface; and
in response to the second communication interface not being communicatively coupled to the third communication interface, storing the tagged first biometric at the data storage;
wherein the directing the second communication interface to wirelessly transmit the tagged first biometric reading is in response to the second communication interface being communicatively coupled to the third communication interface.

15. The system of claim 10, wherein the third communication interface is configured to communicate a confirmation indicating the receipt of the tagged first biometric reading to the second communication interface.

16. The system of claim 15, wherein the data storage is further configured to store the tagged first biometric reading until the second communication interface receives the confirmation.

17. The system of claim 15, wherein the operations further comprise in response to receiving the confirmation, direct the second communication interface to communicate an indication of the confirmation to the first communication interface, and wherein the biometric sensing device further comprises a second data storage configured to store the first biometric reading until the first communication interface receives the indication.

18. The system of claim 10, wherein the operations further comprise direct the second communication interface to wirelessly transmit the identifier to the first communication interface based on the first biometric reading being of the user, and wherein the biometric sensing device further comprises a second data storage configured to store the first biometric reading and the identifier.

19. The system of claim 10, wherein the biometric sensing device comprises:
a second processor configured to execute second instructions to perform second operations, the second operations comprising:
encrypt the first biometric reading; and
direct the first communication interface to wirelessly transmit the encrypted first biometric reading to a fifth communication interface of a second mobile biometric-data hub associated with a third user
a second data storage configured to store the second instructions and the encrypted first biometric reading.

* * * * *